US012600993B2

(12) United States Patent (10) Patent No.: US 12,600,993 B2
Harada et al. (45) Date of Patent: Apr. 14, 2026

(54) METHOD FOR PRODUCING POLY(3-HYDROXYALKANOATE)

(71) Applicant: KANEKA CORPORATION, Osaka (JP)

(72) Inventors: Ken Harada, Hyogo (JP); Shunsuke Sato, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 380 days.

(21) Appl. No.: 18/133,912

(22) Filed: Apr. 12, 2023

(65) Prior Publication Data

US 2023/0265468 A1 Aug. 24, 2023

Related U.S. Application Data

(63) Continuation of application No. PCT/JP2021/037464, filed on Oct. 8, 2021.

(30) Foreign Application Priority Data

Oct. 12, 2020 (JP) ................................. 2020-171770

(51) Int. Cl.
| | |
|---|---|
| *C12P 7/625* | (2022.01) |
| *C12P 5/00* | (2006.01) |
| *C12P 7/6409* | (2022.01) |
| *C12N 1/20* | (2006.01) |

(52) U.S. Cl.
CPC ....... *C12P 7/625* (2013.01); *C10L 2200/0469* (2013.01); *C12N 1/20* (2013.01); *C12P 5/00* (2013.01); *C12P 7/6409* (2013.01)

(58) Field of Classification Search
CPC .. C12N 1/20; C12P 5/00; C12P 7/6409; C12P 7/625; C10L 2200/0469; C12R 2001/01
See application file for complete search history.

(56) References Cited

U.S. PATENT DOCUMENTS

| | | | |
|---|---|---|---|
| 7,384,766 B2 * | 6/2008 | Maruyama ............. | C12N 15/52 |
| | | | 435/69.1 |
| 10,533,197 B2 * | 1/2020 | Fujiki .................. | C12N 9/1029 |

FOREIGN PATENT DOCUMENTS

| | | | | |
|---|---|---|---|---|
| EP | 1557460 A1 * | 7/2005 | ............. | C12P 7/625 |
| JP | 2013-510572 A | 3/2013 | | |
| WO | 2011060048 A2 | 5/2011 | | |
| WO | 2012165131 A1 | 12/2012 | | |

OTHER PUBLICATIONS

Tamang et al. "Valorisation of waste cooking oil using mixed culture into short-and medium-chain length polyhydroxyalkanoates: effect of concentration, temperature and ammonium." Journal of Biotechnology 342 (2021) 92-101 (Year: 2021).*
Cruz et al. "Valorization of fatty acids-containing wastes and byproducts into short-and medium-chain length polyhydroxyalkanoates " New biotechnology 33, No. 1 (2016): 206-215 (Year: 2016).*
International Search Report issued in corresponding International Application No. PCT/JP2021/037464 mailed Dec. 21, 2021 (5 pages).
Written Opinion issued in corresponding International Application No. PCT/JP2021/037464 mailed Dec. 21, 2021 (3 pages).
Office Action issued in counterpart Japanese Patent Application No. 2022-556944 mailed Jul. 29, 2025 (11 pages).

* cited by examiner

*Primary Examiner* — Terry A Mckelvey
*Assistant Examiner* — Andrew T Moehlman
(74) *Attorney, Agent, or Firm* — Osha Bergman Watanabe & Burton LLP

(57) ABSTRACT

In culturing a poly(3-hydroxyalkanoate)-producing microorganism, an oil A and an oil B are used as the carbon source. The proportion of the oil B to the total amount of the oils A and B used during the entire course of the culturing is 10 wt % or more. The oil A is the total oil used until the amount of the poly(3-hydroxyalkanoate) accumulated in the poly(3-hydroxyalkanoate)-producing microorganism reaches 16 wt %, and the average unsaturated fatty acid content in constituent fatty acids is from 25 wt % to less than 75 wt % in the total oil A. The unsaturated fatty acid content in constituent fatty acids in the oil B is higher than the average unsaturated fatty acid content in the total oil A.

10 Claims, No Drawings

METHOD FOR PRODUCING POLY(3-HYDROXYALKANOATE)

TECHNICAL FIELD

One or more embodiments of the present invention relate to a method for producing a poly(3-hydroxyalkanoate) by culturing a poly(3-hydroxyalkanoate)-producing microorganism.

BACKGROUND

Poly(3-hydroxyalkanoates) (also referred to as "PHAs" hereinafter) are biopolyesters that microorganisms store in their cells. Poly(3-hydroxyalkanoates) are used as plastic materials and, in recent years, have attracted attention as environmentally benign materials since they are biodegradable after use.

A method for PHA production is to culture a microorganism having PHA-producing ability and allow the microorganism to accumulate the PHA. This culture requires supplying the microorganism with a carbon source that is suitably assimilated by the microorganism. Typical examples of the carbon source include sugars, oils, and free fatty acids.

For example, Patent Literature 1 describes culturing a microorganism having PHA-producing ability using palm oil as a carbon source.

PATENT LITERATURE

PTL 1: Japanese Laid-Open Patent Application Publication (Translation of PCT Application) No. 2013-510572

Culturing a PHA-producing microorganism using palm oil as a carbon source is known to allow for efficient PHA production. However, palm oil is a relatively expensive oil, and there is a demand for PHA production that uses an easily-available oil as a carbon source instead of palm oil.

Culture of a PHA-producing microorganism was attempted using different oils as carbon sources. As a result, it has been found that there are oils the use of which yields a PHA production rate similar to that achieved with the use of palm oil and that there are oils the use of which results in a clearly lower PHA production rate than the use of palm oil. It has also been found that the oils the use of which results in a low PHA production rate are, in general, oils in which the unsaturated fatty acid content in their constituent fatty acids is relatively high.

Such oils having a relatively high unsaturated fatty acid content are widely used for food purposes, and examples of the oils include rapeseed oil. A large amount of edible oils are discarded after use. In terms of effective use of such edible oils, it is desirable to use oils having a relatively high unsaturated fatty acid content as carbon sources in PHA production.

In view of the above circumstances, one or more embodiments of the present invention aim to achieve a high PHA production rate in PHA production by culture of a PHA-producing microorganism while using an oil having a relatively high unsaturated fatty acid content as a carbon source.

SUMMARY

The present inventors have found that in the case where both an oil A such as palm oil which has a relatively low unsaturated fatty acid content and an oil B such as rapeseed oil which has a relatively high unsaturated fatty acid content are used as carbon sources for a PHA-producing microorganism and where the oil A is used at the early stage of the culture, a high PHA production rate similar to that attained with the use of the oil A alone can be achieved despite the use of the oil B. Based on this finding, the inventors have arrived at one or more embodiments of the present invention.

Specifically, one or more embodiments of the present invention relate to a method for producing a poly(3-hydroxyalkanoate), the method including culturing a poly(3-hydroxyalkanoate)-producing microorganism in the presence of a carbon source, wherein in the culturing, an oil A and an oil B are used as the carbon source, a proportion of the oil B to a total amount of the oils A and B used during an entire course of the culturing is 10 wt % or more, the oil A is a total oil used until an amount of the poly(3-hydroxyalkanoate) accumulated in the poly(3-hydroxyalkanoate)-producing microorganism reaches 16 wt %, and an average unsaturated fatty acid content in constituent fatty acids is from 25 wt % to less than 75 wt % in the total oil A, and an unsaturated fatty acid content in constituent fatty acids in the oil B is higher than the average unsaturated fatty acid content in the total oil A.

Preferably, the carbon source used after a time point at which the amount of the poly(3-hydroxyalkanoate) accumulated in the poly(3-hydroxyalkanoate)-producing microorganism is more than 16 wt % and less than 85 wt % is the oil B.

The oil B is an oil in which the unsaturated fatty acid content may be from 60 to 98 wt %.

The proportion of the oil B to the total amount of the oils A and B used during the entire course of the culturing may be 40 wt % or more.

Preferably, the culturing of the poly(3-hydroxyalkanoate)-producing microorganism is performed until the amount of the poly(3-hydroxyalkanoate) accumulated in the poly(3-hydroxyalkanoate)-producing microorganism reaches 80 wt % or more.

The culturing of the poly(3-hydroxyalkanoate)-producing microorganism may be performed with consecutive addition of the oil A and/or the oil B to a culture medium containing the poly(3-hydroxyalkanoate)-producing microorganism.

Preferably, the culturing of the poly(3-hydroxyalkanoate)-producing microorganism is first performed with consecutive addition of the oil A to a culture medium containing the poly(3-hydroxyalkanoate)-producing microorganism and is then continued with consecutive addition of the oil B to the culture medium.

The poly(3-hydroxyalkanoate) may include at least 3-hydroxybutyrate units.

The poly(3-hydroxyalkanoate) may include a homopolymer of 3-hydroxybutyrate units or a copolymer of 3-hydroxybutyrate units and other hydroxyalkanoate units. The other hydroxyalkanoate units may be 3-hydroxyhexanoate units.

The poly(3-hydroxyalkanoate)-producing microorganism may be a bacterium. The poly(3-hydroxyalkanoate)-producing microorganism may be a bacterium of the genus *Cupriavidus*.

One or more embodiments of the present invention make it possible to achieve a high PHA production rate in PHA production by culture of a PHA-producing microorganism while using an oil having a relatively high unsaturated fatty acid content as a carbon source.

DETAILED DESCRIPTION

Hereinafter, aspects of one or more embodiments of the present invention will be described in detail. One or more embodiments of the present invention are not limited to the aspects of one or more embodiments described below.

One or more embodiments relate to a method for producing a PHA by culturing a PHA-producing microorganism in the presence of a carbon source.

The PHA in the present disclosure is not limited to a particular type and may be any poly(3-hydroxyalkanoate) that can be microbially produced. The PHA may be a homopolymer of one monomer selected from 3-hydroxyalkanoates having 4 to 16 carbon atoms, a copolymer of at least one monomer selected from 3-hydroxyalkanoates having 4 to 16 carbon atoms and another hydroxyalkanoate (such as a 4-hydroxyalkanoate having 4 to 16 carbon atoms or lactic acid), or a copolymer of two or more monomers selected from 3-hydroxyalkanoates having 4 to 16 carbon atoms. Specific examples of the PHA include, but are not limited to, P (3HB) which is a homopolymer of 3-hydroxybutyrate (abbreviated as "3HB"), P (3HB-co-3HV) (abbreviated as "PHBV") which is a copolymer of 3HB and 3-hydroxyvalerate (abbreviated as "3HV"), P (3HB-co-3HH) (abbreviated as "PHBH") which is a copolymer of 3HB and 3-hydroxyhexanoate (abbreviated as "3HH"), P (3HB-co-4HB) which is a copolymer of 3HB and 4-hydroxybutyrate (abbreviated as "4HB"), and a PHA containing lactic acid (abbreviated as "LA") as a constituent (an example of this PHA is P (LA-co-3HB) which is a copolymer of 3HB and LA).

The PHA may be a PHA containing at least 3-hydroxybutyrate units in terms of using the polymer in a wide range of applications. The PHA may be a homopolymer of 3-hydroxybutyrate units or a copolymer of 3-hydroxybutyrate units and other hydroxyalkanoate units. Among the copolymers mentioned above, PHBV and PHBH are more preferred, and PHBH is particularly preferred.

The type of the PHA to be produced can be chosen as appropriate depending on the type of the PHA synthase gene possessed by or introduced into the microorganism used, the type of the metabolic gene involved in the PHA synthesis, the culture conditions, and other factors.

The PHA-producing microorganism is not limited to a particular type and may be any microorganism having PHA-producing ability. The PHA-producing microorganism may be a naturally occurring microorganism, a mutant microorganism, or a transformed microorganism. Specific examples include: bacteria of the genus *Cupriavidus* such as *Cupriavidus* necator: bacteria of the genus *Alcaligenes* such as *Alcaligenes latus*: bacteria of the genus *Pseudomonas* such as *Pseudomonas putida, Pseudomonas fluorescens, Pseudomonas aeruginosa, Pseudomonas resinovorans*, and *Pseudomonas oleovorans*: bacteria of the genus *Bacillus* such as *Bacillus megaterium*: bacteria of the genus *Azotobacter*: bacteria of the genus *Nocardia*: bacteria of the genus *Aeromonas* such as *Aeromonas caviae* and *Aeromonas hydrophila*; bacteria of the genus *Ralstonia*: bacteria of the genus Wautersia; and bacteria of the genus Comamonas (Microbiological Reviews, pp. 450-472, 1990). Biological cells can also be used which have been artificially modified by introducing a PHA synthase gene through a genetic engineering technique and which have thus gained the ability to produce a PHA. For example, the following organisms can be used: gram-negative bacteria such as bacteria of the genus *Escherichia*: gram-positive bacteria such as bacteria of the genus *Bacillus*: yeasts such as yeasts of the genus *Saccharomyces, Yarrowia*, or *Candida*; and cells of higher organisms such as plants. Bacteria are preferred since they can accumulate a large amount of PHA. Bacteria of the genus *Cupriavidus* are particularly preferred.

The PHA synthase gene introduced through genetic transformation is not limited to a particular type. Examples of the PHA synthase gene include: PHA synthase genes derived from *Aeromonas caviae, Aeromonas hydrophila, Pseudomonas* SP 61-3, and *Cupriavidus* necator; and altered genes resulting from alteration of these PHA synthase genes. The term "altered gene" refers to a base sequence that encodes a PHA synthase having an amino acid sequence in which one or more amino acid residues are deleted, added, inserted, or replaced.

Culturing the PHA-producing microorganism in the presence of a carbon source allows the microorganism to accumulate the PHA in its cells. An oil is used as the carbon source. A carbon source other than the oil may be used in combination with the oil.

The oil contains a triglyceride which is an ester of constituent fatty acids with glycerin. The constituent fatty acids may include an unsaturated fatty acid having one or more unsaturated carbon-carbon bonds and/or a saturated fatty acid having no unsaturated carbon-carbon bond. The oil used is not limited to a particular type and may be, for example, an animal oil, a vegetable oil, a mixture of animal and vegetable oils, a transesterified oil, or a fractionated oil. Specific examples of the vegetable oil include rapeseed oil, sunflower oil, soybean oil, olive oil, corn oil, palm oil, palm kernel oil, cottonseed oil, sesame oil, nut oil, Jatropha oil, and rice oil. Specific examples of the animal oil include lard. One of the above-mentioned oils may be used alone, or a mixture of two or more thereof may be used.

The constituent fatty acids of the oil include a short-chain fatty acid having 2 to 4 carbon atoms, a medium-chain fatty acid having 5 to 12 carbon atoms, and a long-chain fatty acid having 12 or more carbon atoms. A preferred oil contains at least three constituent fatty acids selected from the group consisting of lauric acid, myristic acid, myristoleic acid, pentadecanoic acid, palmitic acid, margaric acid, stearic acid, oleic acid, linoleic acid, erucic acid, and linolenic acid. A particularly preferred oil contains at least two constituent fatty acids selected from the group consisting of palmitoleic acid, heptadecanoic acid, oleic acid, linoleic acid, linolenic acid, and erucic acid.

In the present embodiment, two types of oils differing in the unsaturated fatty acid content in constituent fatty acids are used as the carbon source. The two types of oils are classified as oils A and B, each of which is defined as follows.

Oil A: The oil A is the total oil used until the amount of the poly(3-hydroxyalkanoate) accumulated in the poly (3-hydroxyalkanoate)-producing microorganism reaches 16 wt %, and the average unsaturated fatty acid content in constituent fatty acids is from 25 wt % to less than 75 wt % in the total oil A.

Oil B: The unsaturated fatty acid content in constituent fatty acids in the oil B is higher than the average unsaturated fatty acid content in the total oil A.

The unsaturated fatty acid content in an oil is the proportion of the unsaturated fatty acid weight to the total weight of fatty acids constituting the oil and can be calculated through measurement of the weights of the constituent fatty acids. The measurement method is as follows: the oil is saponified with a strong alkali to form free fatty acids: the carboxyl groups of the fatty acids are methyl-esterified to increase the volatility; and the fatty acids are evaporated and separated from one another by gas chromatography to identify the saturated and unsaturated fatty acids.

(Oil A)

The oil A is the total oil used until the amount of the poly(3-hydroxyalkanoate) accumulated in the poly(3-hydroxyalkanoate)-producing microorganism reaches 16 wt %, and the average unsaturated fatty acid content in the total oil A is from 25 wt % to less than 75 wt %. The average unsaturated fatty acid content may be from 30 to 70 wt %, from 40 to 65 wt %, or from 50 to 60 wt %.

For the oil A, the average content of palmitic acid in the total oil A may be from 20 to 65 wt %, from 25 to 60 wt %, or from 30 to 55 wt %.

The oil A may, for example, consist of one available oil such as a vegetable oil or may include two or more available oils insofar as the oil A meets the requirement concerning the average unsaturated fatty acid content. Examples of oils that can be used alone as the oil A include palm oil and lard.

In the case where the oil A includes two or more oils, the total oil A meets the above-described requirement concerning the average unsaturated fatty acid content. The unsaturated fatty acid content in each of the oils constituting the oil A is not limited to a particular range and need not be from 25 wt % to less than 75 wt %. In the case where the oil A includes two or more oils, a mixture of the two or more oils may be added to the culture medium, or the two or more oils may be added to the culture medium simultaneously or sequentially without being mixed.

The "culture of a poly(3-hydroxyalkanoate)-producing microorganism" according to the present embodiment refers to "main culture" finally carried out to allow the poly(3-hydroxyalkanoate)-producing microorganism to accumulate the poly(3-hydroxyalkanoate) to a high concentration. "Pre-culture" and "seed culture" preceding the "main culture" are not included in the "culture" according to the present embodiment. Thus, the carbon sources used in the "preculture" and "seed culture" are not included in the "oil A".

(Oil B)

The oil B is a carbon source used after a time point at which the amount of the poly(3-hydroxyalkanoate) accumulated in the poly(3-hydroxyalkanoate)-producing microorganism is more than 16 wt %, and the unsaturated fatty acid content in the oil B is higher than the average unsaturated fatty acid content in the total oil A. The difference between the unsaturated fatty acid content (wt %) in the oil B and the average unsaturated fatty acid content (wt %) in the total oil A is not limited to a particular range. In terms of enhancing the effect of the combined use of the oils A and B, the difference may be 5 wt % or more, 10 wt % or more, or 20 wt % or more.

The unsaturated fatty acid content in the oil B is defined depending on the relation with the average unsaturated fatty acid content in the total oil A used in combination with the oil B, and is not limited to a specific value. The specific value of the unsaturated fatty acid content in the oil B may be any value higher than the average unsaturated fatty acid content in the total oil A used in combination with the oil B, and may be 75 wt % or more or may be from 25 wt % to less than 75 wt %. For example, as in Example 8 described later, the oil B having an unsaturated fatty acid content of 66 wt % can be used in combination with the oil A having an unsaturated fatty acid content of 58 wt %.

In a preferred aspect, the unsaturated fatty acid content in the oil B may be from 60 to 98 wt %, from 65 to 96 wt %, from 70 to 95 wt %, or from 75 to 94 wt %.

The oil B may, for example, consist of one available oil such as a vegetable oil or may include two or more available oils insofar as the unsaturated fatty acid content in the oil B is higher than the average unsaturated fatty acid content in the total oil A. Examples of oils that can be used as the oil B include rapeseed oil. The oil B may be, for example, a waste edible oil insofar as the oil meets the requirement described above.

A study by the present inventors has revealed that if the oil B having a relatively high unsaturated fatty acid content is used alone as the carbon source in the culture of the PHA-producing microorganism, the PHA production rate slows down.

However, in the present embodiment, a satisfactory PHA production rate can be achieved by using the oils A and B in combination under given conditions. This allows for effective use of the oil B as the carbon source for the PHA-producing microorganism. In terms of effective use of the oil B, the proportion of the oil B may be high. Specifically, the proportion of the oil B to the total amount of the oils A and B used during the entire course of the culture is 10 wt % or more and may be 40 wt % or more, 60 wt % or more, or 80 wt % or more. The upper limit of the proportion of the oil B is not limited to a particular value, but the proportion of the oil B may be 97 wt % or less, 95 wt % or less, or 90 wt % or less. Even when the oil B is used in a high proportion as described above, a high PHA production rate similar to that attained with the use of the oil A alone can be achieved.

The proportion of the oil A to the total amount of the oils A and B used during the entire course of the culture is not limited to a particular range. In terms of increasing the PHA production rate, the proportion of the oil A may be 3 wt % or more, may be 5 wt % or more, may be 10 wt % or more. As to the upper limit, the proportion of the oil A is 90 wt % or less and may be 60 wt % or less, 40 wt % or less, or 20 wt % or less.

(How to Use Carbon Source)

According to the present embodiment, in the culture of the PHA-producing microorganism, the oil A having a relatively low unsaturated fatty acid content is used as the carbon source at least until the amount of the poly(3-hydroxyalkanoate) accumulated in the microorganism reaches 16 wt %. After a time point at which the amount of the accumulated poly(3-hydroxyalkanoate) is more than 16 wt %, the oil B having a relatively high unsaturated fatty acid content is used as the carbon source.

By using the oil A at the early stage of the culture and subsequently using the oil B, a high PHA production rate can be achieved despite the use of the oil B which causes a slow PHA production rate when used alone. Although the mechanism for this effect remains to be elucidated, a possible reason is that: the proliferation of the PHA-producing microorganism is favored over the PHA accumulation at the early stage of the culture, and the oil A having a relatively low unsaturated fatty acid content is more suitable as the carbon source at the cell proliferation stage; and after the proliferation reaches a certain level and the PHA accumulation comes to be favored over the proliferation, the influence of the type of the carbon source is reduced, and the oil B can serve effectively as the carbon source.

After the amount of the accumulated PHA exceeds 16 wt %, the use of an oil having the same unsaturated fatty acid content as the oil A may be continued for a certain period of time. At a time point after the amount of the accumulated PHA exceeds 16 wt %, the carbon source is changed to the oil B having a relatively high unsaturated fatty acid content. In a preferred aspect, the carbon source used after a time point at which the amount of the PHA accumulated in the PHA-producing microorganism is more than 16 wt % and less than 85 wt % may be the oil B. In this case, the oil B, which causes a slow PHA production rate when used alone, can be effectively used as the carbon source in the culture of the PHA-producing microorganism. The amount of the PHA accumulated in the PHA-producing microorganism may be from 20 to 80 wt %, from 25 to 50 wt %, from 25 to 45 wt %, or from 30 to 40 wt %.

The amount of the PHA accumulated in the PHA-producing microorganism can be determined as follows: a given amount of the culture fluid is collected and mixed with an organic solvent to remove the oils, the microbial cells are then washed with water and dried, the weight of the dried microbial cells and the weight of the PHA collected from the same amount of the culture fluid are measured, and the amount of the accumulated PHA is calculated by the following equation.

> Amount of accumulated PHA (%)=[weight (g) of PHA collected from given amount of culture fluid]/[weight (g) of dried microbial cells obtained from given amount of culture fluid]× 100

In a preferred aspect of the present embodiment, it is preferable to start the culture in the presence of the oil A, change the type of the carbon source in the course of the culture (before the amount of the PHA accumulated in the PHA-producing microorganism reaches a final level), then continue the culture in the presence of the oil B, and end the culture at the moment when the amount of the PHA accumulated in the PHA-producing microorganism reaches the final level. By using the oil A as the carbon source at the early stage of the culture and beginning to use the oil B as the carbon source in the course of the culture, a high PHA production rate can easily be achieved despite the fact that the oil B, which causes a slow PHA production rate when used alone, is used as the carbon source.

In the preferred aspect, the timing of changing the carbon source from the oil A to the oil B is not limited to a particular time point and may be chosen as appropriate depending on the amount of the PHA accumulated in the PHA-producing microorganism, the proportion of the oil B used, and other factors. For example, the change of the type of the carbon source may be made, for example, at a time point at which the amount of the PHA accumulated in the PHA-producing microorganism is more than 16 wt % and less than 85 wt %, preferably at a time point at which the amount of the PHA accumulated in the PHA-producing microorganism is from 20 to 80 wt %, more preferably at a time point at which the amount of the PHA accumulated in the PHA-producing microorganism is from 25 to 50 wt %, even more preferably at a time point at which the amount of the PHA accumulated in the PHA-producing microorganism is from 30 to 45 wt %, and particularly preferably at a time point at which the amount of the PHA accumulated in the PHA-producing microorganism is from 30 to 40 wt %. By changing the type of the carbon source at the timing as described above, it is possible to achieve a high PHA production rate while increasing the proportion of the oil B used.

The amount of the PHA accumulated in the PHA-producing microorganism at the end of the culture is not limited to a particular range and may be chosen as appropriate. The amount of the accumulated PHA at the end of the culture may be 80 wt % or more or 90 wt % or more.

The way of adding the oil A or B to a culture medium containing the PHA-producing microorganism may be one-time addition or consecutive addition and may be consecutive addition. That is, the PHA-producing microorganism may be cultured with consecutive addition of the oil A and/or oil B to a culture medium containing the PHA-producing microorganism. The term "consecutive addition" as used herein is intended to include the case of adding the oil continuously without any interruption and the case of adding the oil intermittently several times at intervals.

In a specific aspect of the consecutive addition, it is preferable to first culture the PHA-producing microorganism while adding the oil A consecutively to the culture medium containing the PHA-producing microorganism and dispersing the oil A in the culture medium, then change the type of the carbon source, and then continue the culture while adding the oil B consecutively to the culture medium and dispersing the oil B in the culture medium.

(Culture Medium)

The culture medium used in the culture of the PHA-producing microorganism may be any liquid culture medium containing nutrient sources conducive to the growth and proliferation of the microorganism. Preferably, the PHA-producing microorganism is mixed with a liquid containing the carbon source as described above, a nitrogen source other than the carbon source, an inorganic salt, and another organic nutrient source and is dispersed by stirring, shaking, or any other means.

Examples of the nitrogen source include ammonium salts such as ammonia, ammonium chloride, ammonium sulfate, and ammonium phosphate and further include peptone, meat extract, and yeast extract. Examples of the inorganic salt include potassium dihydrogen phosphate, disodium hydrogen phosphate, magnesium phosphate, magnesium sulfate, and sodium chloride. Examples of the other organic nutrient source include: amino acids such as glycine, alanine, serine, threonine, and proline; and vitamins such as vitamin B1, vitamin B12, and vitamin C.

The culture medium containing the nutrient sources as described above, the carbon source, and the PHA-producing microorganism are dispersed in a vessel to obtain a culture fluid. The culture conditions may be set as per common microbial culture, except for the carbon source described above and the way of adding the carbon source. There are no particular limitations on the culture scale, the aeration/stirring conditions, the culture temperature, the pH during culture, the culture time, etc.

(Collection of PHA)

After the microorganism is cultured for a suitable time to allow the microorganism to accumulate the PHA in its cells, the PHA is collected from the microbial cells using a known technique. The collection of the PHA is not limited to a particular technique and can be accomplished, for example, as follows. After the end of the culture, the microbial cells are separated from the culture fluid by means such as a centrifuge, and the separated microbial cells are washed with a liquid such as distilled water or methanol and then dried. The PHA is extracted from the dried microbial cells using an organic solvent such as chloroform. The cellular components are removed from the PHA-containing solution through a process such as filtration, and a poor solvent such as methanol or hexane is added to the filtrate to precipitate the PHA. The supernatant fluid is removed through filtration or centrifugation, and the PHA is dried and collected.

In another example, the microbial cells are separated from the culture fluid by means such as a centrifuge, and the separated microbial cells are washed with a liquid such as distilled water or methanol. Subsequently, the washed sample is mixed with a solution of sodium lauryl sulfate (SDS), and the mixture is subjected to ultrasonic disruption to break the cell membranes. The cellular components and the PHA are then separated by means such as a centrifuge, and the PHA is dried and collected.

According to the present embodiment, a PHA can be produced at a satisfactory production rate despite the use of an oil which has a relatively high unsaturated fatty acid content and which causes a slow PHA production rate when used alone.

EXAMPLES

Hereinafter, one or more embodiments of the present invention will be described in more detail using examples. One or more embodiments of the present invention are not limited to the examples given below.
(Oils Used)

Oils 1 to 11 used in Examples, Comparative Examples, and Reference Examples described below are listed in Table 1, which shows for each oil the contents of constituent fatty acids, the total saturated fatty acid content, and the total unsaturated fatty acid content. The oil 1 is palm oil, the oil 3 is rapeseed oil, and the oil 10 is lard.

Comparative Examples 1 to 7 and Reference Examples 1 to 4

KNK-005 (see U.S. Pat. No. 7,384,766) was used as the PHA-producing microorganism, and (1) preculture, (2) seed culture, and (3) main culture were sequentially carried out by the procedures described below. In the main culture, each of the oils listed in Table 2 was used alone as the carbon source.
(1) Preculture First, 20 µl of glycerol stock of KNK-005 was inoculated into 20 mL of a preculture medium and cultured at 30° C. for 18 hours.

The preculture medium was composed of 1 w/v % Meat-extract, 1 w/v % Bacto-Tryptone, 0.2 w/v % Yeast-extract, 0.9 w/v % $Na_2HPO_4 \cdot 12H_2O$, and 0.15 w/v % $KH_2PO_4$ (pH=6.8).

TABLE 1

| Constituent fatty acids (Units: wt %) | Oil 1 | Oil 2 | Oil 3 | Oil 4 | Oil 5 | Oil 6 | Oil 7 | Oil 8 | Oil 9 | Oil 10 | Oil 11 |
|---|---|---|---|---|---|---|---|---|---|---|---|
| Myristic acid (14) | 1 | 0 | 0 | 0 | 0.2 | 0.2 | 0.1 | 0.5 | 2.3 | 1.4 | 1.1 |
| Myristoleic acid (14:1) | 0 | 0 | 0 | 0 | 0 | 0 | 0 | 0 | 0.6 | 0.2 | 0 |
| Pentadecanoic acid (15) | 0 | 0 | 0 | 0 | 0 | 0 | 0 | 0 | 0.5 | 0.1 | 0 |
| Palmitic acid (16) | 39.6 | 3.8 | 4 | 6.2 | 9.5 | 9.5 | 10.4 | 19.2 | 19 | 30.3 | 43 |
| Palmitoleic acid (16:1) | 0.2 | 0.2 | 0 | 0.3 | 0.3 | 0.2 | 0.3 | 0.4 | 2.4 | 1.3 | 0.2 |
| Margaric acid (17) | 0 | 0 | 0 | 0 | 0 | 0 | 0 | 0 | 1.5 | 0.8 | 0 |
| Heptadecenoic acid (17:1) | 0 | 0 | 0 | 0 | 0 | 0 | 0 | 0 | 0.6 | 0.3 | 0 |
| Stearic acid (18) | 4.4 | 2 | 2 | 2.5 | 2.3 | 2.3 | 3.7 | 3.5 | 10.7 | 8.5 | 4.5 |
| Oleic acid (18:1) | 42.7 | 75.4 | 53 | 67.2 | 54 | 54.4 | 32.5 | 46.3 | 50.5 | 45.7 | 40.8 |
| Linoleic acid (18:2) | 11.2 | 14.1 | 26 | 19.1 | 26.1 | 25.6 | 44.7 | 25 | 7.8 | 9.2 | 9.1 |
| Linolenic acid (18:3) | 0.2 | 2.1 | 13 | 2.5 | 5.9 | 5.9 | 6.9 | 3.4 | 2.9 | 1.2 | 0.2 |
| Arachidic acid (20) | 0.4 | 0.6 | 0 | 0.5 | 0.5 | 0.5 | 0.4 | 0.4 | 0.3 | 0.3 | 0.4 |
| Erucic acid (20:1) | 0.2 | 1.1 | 2 | 1 | 0.8 | 0.8 | 0.5 | 0.5 | 0.6 | 0.4 | 0.2 |
| (22-24) | 0 | 0.7 | 0 | 0.7 | 0.4 | 0.6 | 0.5 | 0.5 | 0.1 | 0.1 | 0.1 |
| Saturated fatty acid content (wt %) | 45 | 6 | 6 | 9 | 13 | 13 | 15 | 24 | 35 | 42 | 49 |
| Unsaturated fatty acid content (wt %) | 55 | 94 | 94 | 91 | 88 | 88 | 85 | 76 | 66 | 58 | 51 |

(How to Calculate Amount of Accumulated PHA)

The amount of the accumulated PHA (wt %) was determined as follows: a given amount of the culture fluid was mixed with an organic solvent, the microbial cells were then washed with water and dried, the weight of the dried microbial cells and the weight of the PHA collected from the same amount of the culture fluid were measured, and the amount of the accumulated PHA was calculated by the following equation.

> Amount of accumulated PHA (%)=[weight (g) of PHA obtained in Example, Comparative Example, or Reference Example of interest]/ [weight (g) of dried microbial cells obtained in Example, Comparative Example, or Reference Example of interest]×100

(How to Calculate PHA Productivity)

The PHA productivity (%) was calculated by the equation given below as the percentage of the weight (g) of the PHA obtained per liter of the culture fluid in Example, Comparative Example, or Reference Example of interest to the weight (g) of the PHA obtained per liter of the culture fluid in Reference Example 1 or 5 where the PHA was produced using only the oil 1. One of Reference Examples 1 and 5 that employed the same PHA-producing microorganism as Example, Comparative Example, or Reference Example of interest was selected as a basis for comparison.

PHA productivity (%)=[weight (g) of PHA obtained in Example, Comparative Example, or Reference Example of interest]/[weight (g) of PHA obtained in Reference Example 1 or 5]×100

(2) Seed Culture

The preculture fluid obtained as above was inoculated at a concentration of 1.0 v/v % into a 3 L jar fermenter (MDL-8C manufactured by B.E. Marubishi Co., Ltd.) containing 1.8 L of a seed culture medium. The fermenter was operated at a culture temperature of 30° C., a stirring speed of 500 rpm, and an aeration of 1.8 L/min, and the seed culture was conducted for 24 hours during which the pH was controlled between 6.5 and 6.6. For the pH control, a 14% aqueous solution of ammonium hydroxide was used.

The seed culture medium was composed of 1.1 w/v % $Na_2HPO_4 \cdot 12H_2O$, 0.19 w/v % $KH_2PO_4$, 1.29 w/v % $(NH_4)_2SO_4$, 0.1 w/v % $MgSO_4 \cdot 7H_2O$, 2.5 w/v % palm olein oil, and 0.5 v/v % trace metal salt solution (solution of 1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$, and 0.012 w/v % $NiCl_2 \cdot 6H_2O$ in 0.1N hydrochloric acid). The carbon source used was palm olein oil, which was added at one time at a concentration of 10 g/L.
(3) Main Culture The seed culture fluid obtained as above was inoculated at a concentration of 5.0 v/v % into a 5 L jar fermenter (Bioneer-Neo manufactured by B.E. Marubishi Co., Ltd.) containing 2.5 L of a main culture medium. The fermenter was operated at a culture temperature of 34° C., a stirring speed of 600 rpm, and an aeration of 6.0 L/min, and the pH was controlled between 6.5 and 6.6. For the pH control, a 25% aqueous solution of ammonium hydroxide was used.

In the main culture, each of the oils listed in Table 2 was intermittently added as the carbon source during the culture period. The main culture was conducted for 48 hours. After the end of the culture, a given amount of the culture fluid was collected, the microbial cells were washed with distilled water and methanol and then vacuum-dried, and the weight of the dried microbial cells was measured. After the microbial cells were washed as described above, the cellular components of the microbial cells were dissolved using SDS, the resulting solution was subjected to ultrasonic disruption to separate the PHA and the cellular components, and then only the PHA was collected to measure the amount of the accumulated PHA. Based on this result, the PHA productivity was calculated. The calculated values of the PHA productivity are shown in Table 2.

The main culture medium was composed of 0.385 w/v % $Na_2HPO_4·12H_2O$, 0.067 w/v % $KH_2PO_4$, 0.291 w/v % $(NH_4)_2SO_4$, 0.1 w/v % $MgSO_4·7H_2O$, 0.5 v/v % trace metal salt solution (solution of 1.6 w/v % $FeCl_3·6H_2O$, 1 w/v % $CaCl_2)·_2H_2O$, 0.02 w/v % $CoCl_2·6H_2O$, 0.016 w/v % $CuSO_4·5H_2O$, and 0.012 w/v % $NiCl_2·6H_2O$ in 0.1N hydrochloric acid), and 0.05 w/v % BIOSPUREX 200K (defoaming agent manufactured by Cognis Japan Ltd.)

TABLE 2

Culture of KNK-005

| | Oil | Unsaturated fatty acid content in oil (wt %) | PHA productivity (%) |
|---|---|---|---|
| Comparative Example 1 | Oil 2 | 94 | 72 |
| Comparative Example 2 | Oil 3 | 94 | 77 |
| Comparative Example 3 | Oil 4 | 91 | 70 |
| Comparative Example 4 | Oil 5 | 88 | 73 |
| Comparative Example 5 | Oil 6 | 88 | 73 |
| Comparative Example 6 | Oil 7 | 85 | 76 |
| Comparative Example 7 | Oil 8 | 76 | 72 |
| Reference Example 1 | Oil 1 | 55 | 100 |
| Reference Example 2 | Oil 10 | 58 | 93 |
| Reference Example 3 | Oil 11 | 51 | 93 |
| Reference Example 4 | Oil 9 | 66 | 83 |

Table 2 reveals the following findings. Each of the oils used in Comparative Examples 1 to 7 had a high unsaturated fatty acid content, and the use of each oil alone as the carbon source resulted in a low PHA productivity of less than 80%. In contrast, each of the oils used in Reference Examples 1 to 4 had a low unsaturated fatty acid content of less than 75 wt %, and the use of each oil alone as the carbon source resulted in a satisfactory PHA productivity of 80% or more.

Example 1

The (1) preculture, (2) seed culture, and (3) main culture were sequentially carried out under the same conditions as in Comparative Examples 1 to 7 and Reference Examples 1 to 4, except for the following differences. First, the main culture was started with intermittent addition of a first oil (oil 1) as the carbon source. Once the amount of the PHA accumulated in the microorganism reached 15 wt %, the carbon source was changed to a second oil (oil 2), and the main culture was continued with intermittent addition of the second oil. The main culture was ended 48 hours after the start of the culture. Table 3 shows the proportions of the first and second oils in the carbon source used in the main culture and the calculated values of the PHA productivity.

In this example, the combination of the entire amount of oil 1 and the slight amount of oil 2 used during the period in which the amount of the accumulated PHA increased from 15 wt % to 16 wt % corresponds to the oil A. In this case, the average unsaturated fatty acid content of the oil A is about 58%. The oil 2 corresponds to the oil B.

Example 2

The (1) preculture, (2) seed culture, and (3) main culture were sequentially carried out under the same conditions as in Example 1, except that the oil 8 was used as the second oil in the main culture. Table 3 shows the proportions of the first and second oils in the carbon source used in the main culture and the calculated values of the PHA productivity.

In this example, the combination of the entire amount of oil 1 and the slight amount of oil 8 used during the period in which the amount of the accumulated PHA increased from 15 wt % to 16 wt % corresponds to the oil A. In this case, the average unsaturated fatty acid content of the oil A is about 56%. The oil 8 corresponds to the oil B.

Examples 3 and 4

The (1) preculture, (2) seed culture, and (3) main culture were sequentially carried out under the same conditions as in Example 1, except that in the main culture, the oils listed in Table 3 were used as the first and second oils, and the carbon source was changed from the first oil to the second oil once the amount of the PHA accumulated in the microorganism reached 20 wt %. Table 3 shows the proportions of the first and second oils in the carbon source used in the main culture and the calculated values of the PHA productivity.

In this example, the first oil (oil 1) corresponds to the oil A, and the second oil (oil 2) corresponds to the oil B. The same applies to Examples 5 to 9 described below.

Examples 5 to 8

The (1) preculture, (2) seed culture, and (3) main culture were sequentially carried out under the same conditions as in Example 1, except that in the main culture, the oils listed in Table 3 were used as the first and second oils, and the carbon source was changed from the first oil to the second oil once the amount of the PHA accumulated in the microorganism reached 30 to 34 wt %. Table 3 shows the proportions of the first and second oils in the carbon source used in the main culture and the calculated values of the PHA productivity.

Example 9

The (1) preculture, (2) seed culture, and (3) main culture were sequentially carried out under the same conditions as in Example 1, except that in the main culture, the carbon source was changed from the first oil to the second oil once the amount of the PHA accumulated in the microorganism reached 79 wt %. Table 3 shows the proportions of the first and second oils in the carbon source used in the main culture and the calculated values of the PHA productivity.

TABLE 3

| | | | Amount of accumulated PHA at time of change | | | Average unsaturated fatty acid | |
| | | Proportion | of carbon source | Type | Proportion | content in | PHA |
| | Type of | of first oil | from first oil to | of second | of second oil | total oil A | productivity |
| | first oil | (wt %) | second oil (wt %) | oil | (wt %) | (wt %) | (%) |
| --- | --- | --- | --- | --- | --- | --- | --- |
| Example 1 | Oil 1 | 5 | 15 | Oil 2 | 95 | 58 | 82 |
| Example 2 | Oil 1 | 5 | | Oil 8 | 95 | 56 | 83 |
| Example 3 | Oil 1 | 8 | 20 | Oil 2 | 92 | 55 | 91 |
| Example 4 | Oil 1 | 7 | | Oil 8 | 93 | 55 | 91 |
| Example 5 | Oil 1 | 13 | 30-34 | Oil 2 | 87 | 55 | 97 |
| Example 6 | Oil 1 | 14 | | Oil 3 | 86 | 55 | 95 |
| Example 7 | Oil 1 | 16 | | Oil 4 | 84 | 55 | 91 |
| Example 8 | Oil 10 | 19 | | Oil 9 | 81 | 58 | 99 |
| Example 9 | Oil 1 | 58 | 79 | Oil 2 | 42 | 55 | 98 |

Table 3 reveals the following findings. In Examples 1 to 9, the main culture was started using the first oil having an unsaturated fatty acid content of 25 wt % to less than 75 wt % as the carbon source, then the carbon source was changed to the second oil having a higher unsaturated fatty acid content than the first oil in the course of the main culture, and the main culture was continued using the second oil. In all of Examples 1 to 9, the PHA productivity was satisfactory and 80% or more. In particular, in Examples 3 to 8, the PHA productivity was considerably high and 90% or more despite the fact that the proportion of the second oil, which caused low PHA productivity when used alone, was 80 wt % or more.

When an oil having a relatively high unsaturated fatty acid content is used alone, the PHA productivity is low as proportions of the oils 1 and 2 in the carbon source used in the main culture and the calculated values of the PHA productivity.

Comparative Example 9

The (1) preculture, (2) seed culture, and (3) main culture were sequentially carried out under the same conditions as in Comparative Example 8, except that in the main culture, the carbon source was changed from the oil 2 to the oil 1 once the amount of the PHA accumulated in the microorganism reached 80 wt %. Table 4 shows the proportions of the oils 1 and 2 in the carbon source used in the main culture and the calculated values of the PHA productivity.

TABLE 4

| | | | Amount of accumulated | | Proportion | Average unsaturated | |
| | | Proportion | PHA at time of change | Type | of | fatty acid | PHA |
| | Type of | of first oil | of carbon source from | of second | second oil | content in | productivity |
| | first oil | (wt %) | first oil to second oil (wt %) | oil | (wt %) | total oil A (wt %) | (%) |
| --- | --- | --- | --- | --- | --- | --- | --- |
| Comparative Example 8 | Oil 2 | 17 | 30 | Oil 1 | 83 | 94 | 76 |
| Comparative Example 9 | Oil 2 | 64 | 80 | Oil 1 | 36 | 94 | 72 | demonstrated by Comparative Examples 1 to 7 and Reference Example 4 listed in Table 2. However, it is seen that satisfactory PHA productivity can be achieved when such an oil and another oil having an unsaturated fatty acid content of 25 wt % to less than 75 wt % are used sequentially.

Comparative Example 8

The (1) preculture, (2) seed culture, and (3) main culture were sequentially carried out under the same conditions as in Example 1, except for the following differences. The order of adding the oils 1 and 2 was reversed from that in the main culture of Example 1, and the main culture was started with intermittent addition of the oil 2 as the carbon source. Once the amount of the PHA accumulated in the microorganism reached 30 wt %, the carbon source was changed to the oil 1, and the main culture was continued with intermittent addition of the oil 1. The main culture was ended 48 hours after the start of the culture. Table 4 shows the Table 4 reveals the following findings. In Comparative Examples 8 and 9, unlike in Examples 1 to 9, the main culture was started using an oil having a relatively high unsaturated fatty acid content (oil 2) as the carbon source, then the carbon source was changed to an oil having an unsaturated fatty acid content of 25 wt % to less than 75 wt % (oil 1) in the course of the main culture, and the main culture was continued using the oil 1. As a result, the PHA productivity was as low as less than 80% and similar to that in Comparative Examples 1 to 7. In particular, in Comparative Example 8, the PHA productivity was very low and 76% despite the fact that the proportion of the oil 1, which effected the highest PHA productivity when used alone, was 80 wt % or more.

The above results have demonstrated that in order to achieve satisfactory PHA productivity, the carbon source used at the early stage of the culture is desirably an oil having an unsaturated fatty acid content of 25 wt % to less than 75 wt % as in Examples 1 to 9, rather than an oil having a relatively high unsaturated fatty acid content.

Comparative Examples 10 to 12 and Reference Examples 5 to 7

The (1) preculture, (2) seed culture, and (3) main culture were sequentially carried out under the same conditions as in Comparative Examples 1 to 7 and Reference Examples 1 to 4, except that *Cupriavidus* necator H16 was used as the PHA-producing microorganism and that each of the oils listed in Table 5 was used alone as the carbon source in the main culture. Table 5 shows the calculated values of the PHA productivity.

TABLE 5

| Culture of H16 | | | |
|---|---|---|---|
| | Oil | Unsaturated fatty acid content in oil (wt %) | PHA productivity (%) |
| Comparative Example 10 | Oil 2 | 94 | 69 |
| Comparative Example 11 | Oil 4 | 91 | 70 |
| Comparative Example 12 | Oil 8 | 76 | 72 |
| Reference Example 5 | Oil 1 | 55 | 100 |
| Reference Example 6 | Oil 10 | 58 | 96 |
| Reference Example 7 | Oil 9 | 66 | 83 |

Table 5 reveals the following findings. In Comparative Examples 10 to 12, where an oil having a relatively high unsaturated fatty acid content was used alone as the carbon source, the PHA productivity was as low as less than 80%. In contrast, in Reference Examples 5 to 7, where an oil having a low unsaturated fatty acid content of less than 75 wt % was used as the carbon source, the PHA productivity was satisfactory and 80% or more. That is, it is seen that the correlation between the type of the carbon source and the PHA productivity in Comparative Examples 10 to 12 and Reference Examples 5 to 7 showed the same trend as in Comparative Examples 1 to 7 and Reference Examples 1 to 4 although the PHA-producing microorganism used in Comparative Examples 10 to 12 and Reference Examples 5 to 7 was different from that used in Comparative Examples 1 to 7 and Reference Examples 1 to 4.

Example 10

The (1) preculture, (2) seed culture, and (3) main culture were sequentially carried out under the same conditions as in Comparative Examples 10 to 12 and Reference Examples 5 to 7, except for the following differences. The main culture was started with intermittent addition of a first oil (oil 1) as the carbon source. Once the amount of the PHA accumulated in the microorganism reached 15 wt %, the carbon source was changed to a second oil (oil 2), and the main culture was continued with intermittent addition of the second oil. The main culture was ended 48 hours after the start of the culture. Table 6 shows the proportions of the first and second oils in the carbon source used in the main culture and the calculated values of the PHA productivity.

Example 11

The (1) preculture, (2) seed culture, and (3) main culture were sequentially carried out under the same conditions as in Example 10, except that the oil 8 was used as the second oil in the main culture. Table 6 shows the proportions of the first and second oils in the carbon source used in the main culture and the calculated values of the PHA productivity.

Examples 12 and 13

The (1) preculture, (2) seed culture, and (3) main culture were sequentially carried out under the same conditions as in Example 10, except that in the main culture, the oils listed in Table 6 were used as the first and second oils, and the carbon source was changed from the first oil to the second oil once the amount of the PHA accumulated in the microorganism reached 20 wt %. Table 6 shows the proportions of the first and second oils in the carbon source used in the main culture and the calculated values of the PHA productivity.

Examples 14 to 18

The (1) preculture, (2) seed culture, and (3) main culture were sequentially carried out under the same conditions as in Example 10, except that in the main culture, the oils listed in Table 6 were used as the first and second oils, and the carbon source was changed from the first oil to the second oil once the amount of the PHA accumulated in the microorganism reached 30 to 34 wt %. Table 6 shows the proportions of the first and second oils in the carbon source used in the main culture and the calculated values of the PHA productivity.

Example 19

The (1) preculture, (2) seed culture, and (3) main culture were sequentially carried out under the same conditions as in Example 10, except that in the main culture, the carbon source was changed from the first oil to the second oil once the amount of the PHA accumulated in the microorganism reached 82 wt %. Table 6 shows the proportions of the first and second oils in the carbon source used in the main culture and the calculated values of the PHA productivity.

TABLE 6

| Culture of H16 | | | | | | | |
|---|---|---|---|---|---|---|---|
| | Type of first oil | Proportion of first oil (wt %) | Amount of accumulated PHA at time of change of carbon source from first oil to second oil (wt %) | Type of second oil | Proportion of second oil (wt %) | Average unsaturated fatty acid content in total oil A (wt %) | PHA productivity (%) |
| Example 10 | Oil 1 | 5 | 15 | Oil 2 | 95 | 58 | 84 |
| Example 11 | Oil 1 | 6 | | Oil 8 | 94 | 56 | 83 |
| Example 12 | Oil 1 | 8 | 20 | Oil 2 | 92 | 55 | 91 |

TABLE 6-continued

| | | | Culture of H16 | | | | |
|---|---|---|---|---|---|---|---|
| | Type of first oil | Proportion of first oil (wt %) | Amount of accumulated PHA at time of change of carbon source from first oil to second oil (wt %) | Type of second oil | Proportion of second oil (wt %) | Average unsaturated fatty acid content in total oil A (wt %) | PHA productivity (%) |
| Example 13 | Oil 1 | 8 | | Oil 8 | 92 | 55 | 90 |
| Example 14 | Oil 1 | 12 | 30-34 | Oil 2 | 88 | 55 | 97 |
| Example 15 | Oil 1 | 17 | | Oil 4 | 83 | 55 | 97 |
| Example 16 | Oil 1 | 18 | | Oil 8 | 82 | 55 | 93 |
| Example 17 | Oil 1 | 18 | | Oil 9 | 82 | 55 | 99 |
| Example 18 | Oil 10 | 19 | | Oil 4 | 81 | 58 | 98 |
| Example 19 | Oil 1 | 54 | 82 | Oil 2 | 46 | 55 | 98 |

Table 6 reveals the following findings. In Examples 10 to 19, as in Examples 1 to 9, the main culture was started using the first oil having an unsaturated fatty acid content of 25 wt % to less than 75 wt % as the carbon source, then the carbon source was changed to the second oil having a relatively high unsaturated fatty acid content in the course of the main culture, and the main culture was continued using the second oil. In all of Examples 10 to 19, the PHA productivity was satisfactory and 80% or more. In particular, in Examples 12 to 18, the PHA productivity was considerably high and 90% or more despite the fact that the proportion of the second oil, which caused low PHA productivity when used alone, was 80 wt % or more.

When an oil having a relatively high unsaturated fatty acid content is used alone, the PHA productivity is low as demonstrated by Comparative Examples 10 to 12 and Reference Example 7 listed in Table 5. However, it is seen that satisfactory PHA productivity can be achieved when such an oil and another oil having an unsaturated fatty acid content of 25 wt % to less than 75 wt % are used sequentially.

Comparative Example 13

The (1) preculture, (2) seed culture, and (3) main culture were sequentially carried out under the same conditions as in Example 10, except for the following differences. The order of adding the oils 1 and 2 was reversed from that in the main culture of Example 10, and the main culture was started with intermittent addition of the oil 2 as the carbon source. Once the amount of the PHA accumulated in the microorganism reached 32 wt %, the carbon source was changed to the oil 1, and the main culture was continued with intermittent addition of the oil 1. The main culture was ended 48 hours after the start of the culture. Table 7 shows the proportions of the oils 1 and 2 in the carbon source used in the main culture and the calculated values of the PHA productivity.

Comparative Example 14

The (1) preculture, (2) seed culture, and (3) main culture were sequentially carried out under the same conditions as in Comparative Example 13, except that in the main culture, the carbon source was changed from the oil 2 to the oil 1 once the amount of the PHA accumulated in the microorganism reached 80 wt %. Table 7 shows the proportions of the oils 1 and 2 in the carbon source used in the main culture and the calculated values of the PHA productivity.

TABLE 7

| | | | Culture of H16 | | | | |
|---|---|---|---|---|---|---|---|
| | Type of first oil | Proportion of first oil (wt %) | Amount of accumulated PHA at time of change of carbon source from first oil to second oil (wt %) | Type of second oil | Proportion of second oil (wt %) | Average unsaturated fatty acid content in total oil A (wt %) | PHA productivity (%) |
| Comparative Example 13 | Oil 2 | 21 | 32 | Oil 1 | 79 | 94 | 73 |
| Comparative Example 14 | Oil 2 | 66 | 80 | Oil 1 | 34 | 94 | 70 |

Table 7 reveals the following findings. In Comparative Examples 13 and 14, unlike in Examples 10 to 19, the main culture was started using an oil having a relatively high unsaturated fatty acid content (oil 2) as the carbon source, then the carbon source was changed to an oil having an unsaturated fatty acid content of 25 wt % to less than 75 wt % (oil 1) in the course of the main culture, and the main culture was continued using the oil 1. As a result, the PHA productivity was as low as less than 80% and similar to that in Comparative Examples 10 to 12. In particular, in Comparative Example 13, the PHA productivity was very low and 73% despite the fact that the proportion of the oil 1, which effected the highest PHA productivity when used alone, was nearly 80 wt %.

The above results have demonstrated that in order to achieve satisfactory PHA productivity, the carbon source used at the early stage of the culture is desirably an oil having an unsaturated fatty acid content of 25 wt % to less than 75 wt % as in Examples 10 to 19, rather than an oil having a relatively high unsaturated fatty acid content.

Although the disclosure has been described with respect to only a limited number of embodiments, those skilled in the art, having benefit of this disclosure, will appreciate that various other embodiments may be devised without departing from the scope of the present disclosure. Accordingly, the scope of the invention should be limited only by the attached claims.

What is claimed is:

1. A method comprising:

culturing a poly(3-hydroxyalkanoate)-producing microorganism in the presence of a carbon source comprising oil, wherein the poly(3-hydroxyalkanoate)-producing microorganism is *Cupriavidus* necator and wherein the culturing comprises:

adding an oil A until an amount of poly(3-hydroxyalkanoate) accumulated in the poly(3-hydroxyalkanoate)-producing microorganism reaches at least 16 wt %, and an average unsaturated fatty acid content in constituent fatty acids is from 25 wt % to less than 75 wt % in the oil A;

stopping adding the oil A; and adding an oil B such that a proportion of oil B to oils A and B added during an entire course of the culturing is 10 wt % or more;

wherein the amount of the poly(3-hydroxyalkanoate) accumulated in the poly(3-hydroxyalkanoate)-producing microorganism is a percentage of a weight of the poly(3-hydroxyalkanoate) collected from a given amount of culture fluid compared to a weight of dried microbial cells obtained from the given amount of culture fluid, and an unsaturated fatty acid content in constituent fatty acids in the oil B is higher than the average unsaturated fatty acid content in the oil A.

2. The method according to claim 1, wherein the oil B is added after a time point at which an amount of the poly(3- hydroxyalkanoate) accumulated in the microorganism is more than 16 wt % and less than 85 wt %.

3. The method according to claim 1, wherein the oil B is an oil in which the unsaturated fatty acid content is from 60 to 98 wt %.

4. The method according to claim 1, wherein the proportion of oil B to oils A and B added during the entire course of the culturing is 40 wt % or more.

5. The method according to claim 1, wherein the culturing of the poly(3-hydroxyalkanoate)-producing microorganism is performed until the amount of the poly(3-hydroxyalkanoate) accumulated in the poly(3-hydroxyalkanoate)-producing-microorganism reaches 80 wt % or more.

6. The method according to claim 1, wherein the culturing of the poly(3-hydroxyalkanoate)-producing microorganism is performed with consecutive addition of the oil A and/or the oil B to a culture medium containing the poly(3-hydroxyalkanoate)-producing microorganism.

7. The method according to claim 1, wherein the culturing of the poly(3-hydroxyalkanoate)-producing microorganism is first performed with consecutive addition of the oil A to a culture medium containing the poly(3-hydroxyalkanoate)-producing microorganism and is then continued with consecutive addition of the oil B to the culture medium.

8. The method according to claim 1, wherein the poly(3-hydroxyalkanoate) comprises 3-hydroxybutyrate units.

9. The method according to claim 1, wherein the poly(3-hydroxyalkanoate) comprises a homopolymer of 3-hydroxybutyrate units or a copolymer of 3-hydroxybutyrate units and other hydroxyalkanoate units.

10. The method according to claim 9, wherein the other hydroxyalkanoate units are 3-hydroxyhexanoate units.

* * * * *